United States Patent [19]

Detty et al.

[11] Patent Number: 4,634,553

[45] Date of Patent: Jan. 6, 1987

[54] NOVEL 4H-TELLURIN TELLURANE ELECTRON-ACCEPTING SENSITIZERS FOR ELECTRON-DONATING PHOTOCONDUCTIVE COMPOSITIONS

[75] Inventors: Michael R. Detty, Rochester; Bruce J. Murray, Walworth; Michael Scozzafava, Rochester, all of N.Y.

[73] Assignee: Eastman Kodak Company, Rochester, N.Y.

[21] Appl. No.: 764,469

[22] Filed: Aug. 12, 1985

[51] Int. Cl.⁴ .................................................. C07D 345/00
[52] U.S. Cl. ............................................ 540/1; 430/83; 430/900

[58] Field of Search .................... 430/83, 900; 260/239

[56] References Cited

U.S. PATENT DOCUMENTS

| | | | |
|---|---|---|---|
| 4,365,017 | 12/1982 | Detty et al. | 430/83 |
| 4,431,586 | 2/1984 | Detty et al. | 260/239 |
| 4,434,098 | 2/1984 | Detty et al. | 260/239 |

*Primary Examiner*—John L. Goodrow
*Attorney, Agent, or Firm*—John R. Everett

[57] ABSTRACT

Novel 4H-tellurin compounds are disclosed. The compounds are useful as electron-accepting sensitizers for electron-donating photoconductive-compositions.

8 Claims, No Drawings

NOVEL 4H-TELLURIN TELLURANE ELECTRON-ACCEPTING SENSITIZERS FOR ELECTRON-DONATING PHOTOCONDUCTIVE COMPOSITIONS

FIELD OF THE INVENTION

The invention relates to novel 4H-tellurin tellurane compounds and their use as electron-accepting sensitizers in electron-donating photoconductive compositions and elements.

BACKGROUND OF THE INVENTION

Photoconductive compositions and elements are well known for use in electrophotographic imaging processes. Some of the most useful photoconductive compositions comprise an electron-donating photoconductive material and a sensitizer for the photoconductor.

SUMMARY OF THE INVENTION

The present invention provides a new class of compounds comprising a 4H-tellurin tellurane nucleus as sensitizers for electron-donating photoconductive compositions. These new sensitizers improve the quantum efficiency and the speed of electron-donating photoconductive compositions. In general, the neutral species (i.e., nonionic) are vacuum coatable.

PREFERRED EMBODIMENT OF THE INVENTION

The preferred compounds of the present invention comprise a 4H-tellurin tellurane nucleus having the structure

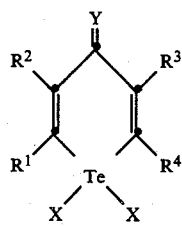

wherein $R^1$ and $R^4$ each independently represent hydrogen, branched or straight chain alkyl, usually containing from 1 to 10 carbon atoms (e.g. methyl, t-butyl, hexyl and nonyl), trialkylsilyl such as trimethyl-, trihexyl- and trinonylsilyl; triarylsilyl such as triphenylsilyl; alkylarylsilyl such as methylphenylsilyl; substituted or unsubstituted aryl such as phenyl and p-methoxyphenyl; and heteroaryl such as 2-thiophenyl;

$R^2$ and $R^3$ each independently represent hydrogen; or $R^1$ and $R^2$, or $R^3$ and $R^4$, taken together with the carbon atoms to which they are attached, form a 4 to 20 carbon atom, mono- or polynuclear fused carbocyclic aromatic ring having at least one electron-donating substituent (e.g. methoxy, fluoro and dimethylamino) meta to the carbon bearing the tellurium atom;

X represents F, Cl, Br, I, OH,

wherein $R^5$ is alkyl or aryl;

Y represents O, S, $C(CN)_2$, $C(COR_5)_2$,

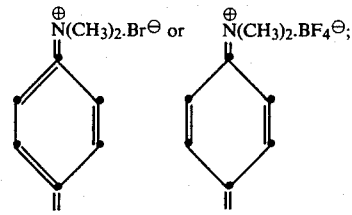

a 4H-tellurin group of the structure

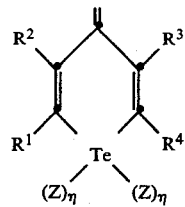

wherein $R^1$, $R^2$, $R^3$ and $R^4$ are as above;

Z represents OH, or

and $\eta$ represents 0 or 1.

DETAILS OF THE INVENTION

In general, preparations of the compounds of the present invention involve one or more of the following two processes:

1. The addition of $Cl_2$, $Br_2$, $I_2$, $CF_3OF$ (an $F_2$ equivalent) or $R_5CO_3H$ to a solution of a telluropyrone compound of the structure

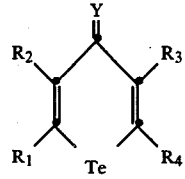

wherein $R_1$ to $R_4$ and Y are as previously defined. Telluropyrone compounds used as a starting material in this method are disclosed in U.S. Pat. Nos. 4,431,586 and 4,434,098.

2. Heating under an oxygen containing atmosphere, an acetonitrile solution of triphenylphospine oxide or triphenylphosphine and a telluropyrylium compound of the structure

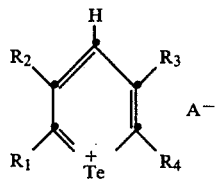

wherein $R_1$ to $R_4$ are as previously defined and A is a negative ion.

The telluropyrylium compounds used as starting materials in this method are disclosed in U.S. Pat. No. 4,365,017.

In both of the above methods, the compounds of the present invention are isolated by conventional procedures such as conventional procedures of concentration, recrystallization, extractive workup and/or chromatography.

The following Examples 1-18 illustrate the above-described methods for making the 4H-tellurin telluranes of the present invention. In each of the following examples (1-16) of the preparation of the compounds in which a telluropyrone starting material was used, the telluropyrone had substituents in the $R_1$, $R_2$, $R_3$, $R_4$ and Y positions as indicated in Table I.

EXAMPLES 1-4

Preparation of Compounds 1, 2, 3 and 4 of Table I

A telluropyranone compound (3.13 mmol) in 5 mL of dichloromethane and 5 mL of acetic acid was cooled to 0° C. Peracetic acid (40% in acetic acid, 1.3 gm, 6.9 mmol) was added slowly. After stirring 5 minutes at 0° C., the reaction mixture was diluted with water (100 mL) and the product was extracted with dichloromethane (3×25 mL). The combined organic extracts were washed with water (3×25 mL) and brine (25 mL), were dried over sodium sulfate and concentrated. The residue was recrystallized to give the corresponding bisacetate.

EXAMPLES 5-12

Preparation of Compounds 5, 6, 7, 8, 9, 10, 11 and 12 of Table I

The bromine (2.0 gm, 6.2 mmol) in 5 mL of dichloromethane was added dropwise to a solution of telluropyranone (5.0 mmol) in 20 mL of dichloromethane. After addition was completed, the reaction mixture was concentrated. Recrystallization of the residue gave the dibromides.

EXAMPLES 13 AND 14

Preparation of Dichlorides 14 and 15 of Table I

Chlorine gas was bubbled into a carbontetrachloride solution (50 mL) of telluropyranone (5.0 mmol) until the solution became colorless. The reaction mixture was concentrated and the residue recrystallized to give the product.

EXAMPLES 15 AND 16

Preparation of Diiodides 16 and 17 of Table I

Iodine (0.25 gm, 1.0 mmol) was added to a stirred solution of the telluropyranone (1.0 mmol) in 10 mL of dichloromethane. After stirring 15 minutes at ambient temperature, the reaction mixture was concentrated. The residue was recrystallized to give the product. The diiodides were quite unstable.

EXAMPLE 17

2-Phenyl-7-methoxybenzo[b]tellurapyrylium perchlorate (0.35 gm, 0.79 mmol) and triphenylphosphine (50 mg) in 2 mL of pyridine were heated 1.5 hours on a steam bath. The reaction mixture was concentrated to dryness. The residue was purified by chromotography on silica gel eluted with $CH_2Cl_2$ to give 0.070 gm (25%) of Compound 20 as a yellow solid, mp 115°-116° C.

EXAMPLE 18

2,6-Diphenyltellurapyrylium fluoroborate (200 mg) and triphenylphosphine oxide (200 mg) in 2 mL of pyridine were heated on a steam bath for 1.5 hours. The reaction mixture was concentrated to dryness. The residue was purified by chromatography on silica gel eluted with $CH_2Cl_2$ to give 105 mg (50%) of Compound 19, mp 134.5°-136.5° C.

The compounds prepared according to the foregoing examples are presented in Table I. Compounds 18 and 22-23 were also prepared by one of the foregoing procedures. Compounds 24-25 could be prepared by one of such methods. Except for compounds 24-25, the structures of each of the compounds in Table I were confirmed by melting points, NMR analysis, infrared spectral analysis, mass spectral analysis and elemental analysis.

TABLE I

4H—Tellurin Telluranes of the Following Structure

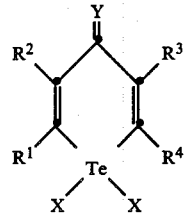

| Compound | $R^1$ | $R^2$ | $R^3$ | $R^4$ | X | Y | mp(°C.) |
|---|---|---|---|---|---|---|---|
| 1 | t-butyl | H | H | t-butyl | $CH_3C(=O)-O$ | O | 161–165 |
| 2 | phenyl | H | H | phenyl | $CH_3C(=O)-O$ | O | 137–141 |
| 3* | phenyl | H | | 7-methoxybenzo | $CH_3C(=O)-O$ | O | 189–191 |

TABLE I-continued
4H—Tellurin Telluranes of the Following Structure

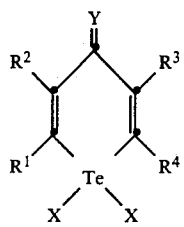

| Compound | R¹ | R² | R³ | R⁴ | X | Y | mp(°C.) |
|---|---|---|---|---|---|---|---|
| 4 | t-butyl | H | H | t-butyl | CH₃C(=O)—O | C(CN)₂ | 131.5–132.5 |
| 5 | t-butyl | H | H | t-butyl | Br | O | 225–227.5 |
| 6 | phenyl | H | H | phenyl | Br | O | 208–210 |
| 7* | phenyl | H |  | 7-methoxybenzo | Br | O | 220–222 |
| 8* | t-butyl | H |  | 7-methoxybenzo | Br | O | 165–170 |
| 9 | t-butyl | H | H | t-butyl | Br | C(CN)₂ | 207–208 |
| 10 | phenyl | H | H | phenyl | Br | C(CN)₂ | 243–244 |
| 11 | t-butyl | H | H | t-butyl | Br | C(CH₃)₂(OC(=O))₂ (isopropylidene malonate) | 153–155.5 |
| 12* | t-butyl | H |  | 7-methoxybenzo | Br | C(CH₃)₂(OC(=O))₂ (isopropylidene malonate) | 170–180(dec) |
| 13 | phenyl | H | H | p-FC₆H₄ | Br | O | 220–222(dec) |
| 14 | t-butyl | H | H | t-butyl | Cl | O | 163.5–166 |
| 15 | t-butyl | H | H | t-butyl | Cl | C(CN)₂ | 218.5–221.5 |
| 16 | t-butyl | H | H | t-butyl | I | O | 114–130(dec) |
| 17 | t-butyl | H | H | t-butyl | I | C(CN)₂ | 110–140(dec) |
| 18 | phenyl | H |  | 7-methoxybenzo | Cl | O | 155–157 |
| 19 | phenyl | H | H | phenyl | O (=O) | Ph–Te–Ph telluranyl | 134.5–136.5 |
| 20* | phenyl | H |  | 7-methoxybenzo | OH | Ph(OH)₂Te-(7-methoxybenzo) | 115–116 |
| 21 | phenyl | H | H | trimethylsilyl | Br | O | 140–145 |

TABLE I-continued
4H—Tellurin Telluranes of the Following Structure

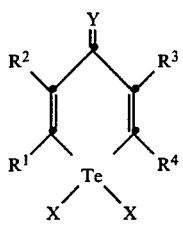

| Compound | R¹ | R² | R³ | R⁴ | X | Y | mp(°C.) |
|---|---|---|---|---|---|---|---|
| 22 | phenyl | H | H | phenyl | Br | ⊕N(CH$_3$)$_2$–C$_6$H$_4$=  BF$_4$⊖ | 222–233 |
| 23 | t-butyl | H | H | t-butyl | Br | ⊕N(CH$_3$)$_2$–C$_6$H$_4$=  Br⊖ | 177–177.5 |

Other compounds which can be made include:

| | | | | | | | |
|---|---|---|---|---|---|---|---|
| 24 | phenyl | H | H | triphenylsilyl | Br | O | |
| 25 | phenyl | H | H | dimethylphenylsilyl | Br | O | |

<sup>a</sup>These are compounds in which R³ and R⁴ taken together with the carbon atoms to which they are attached form a fused methoxybenzo group in which the methoxy group is meta to the carbon atom to which the Te atom is attached or more specifically, in the 7-position of the resulting 4H—tellurin nucleus.

The present invention provides photoconductive compositions and elements in which organic electron donor-type photoconductors are combined with sensitizing amounts of the 4H-tellurin tellurane sensitizers of the present invention.

The compositions are generally prepared by blending a dispersion or solution of the donor-type photoconductor together with an electrically insulating, film-forming resin binder, when necessary or desirable, and coating the compositions on a support or forming a self-supporting layer with the photoconductive composition. Generally, a sensitizing amount of the sensitizing compound is mixed with the photoconductive coating composition so that, after thorough mixing, the sensitizer is uniformly distributed throughout a layer formed from the composition. The amount of sensitizer which can be added to a photoconductive composition layer to give effective increases in sensitivity vary widely. The optimum concentration in any given case varies with the specific donor and acceptor used.

In general, an appropriate sensitizer is added in a concentration range from about 0.001 to about 30 percent by weight based on the weight of the film forming coating composition. Generally, the sensitizer is added to the coating composition in an amount from about 0.05 to about 10 percent by weight of the total coating composition.

The sensitizers are effective in enhancing the photosensitivity of a wide variety of donor-type photoconductors especially those containing a tertiary amine component. Useful photoconductors are described below.

(1) arylamine photoconductors including substituted and unsubstituted arylamines, diarylamines, nonpolymeric triarylamines and polymeric triarylamines such as those described in U.S. Pat. Nos. 3,240,597 by Fox issued Mar. 15, 1966, and 3,180,730 by Klupfel et al issued Apr. 27, 965;

(2) polyarylalkane photoconductors of the types described in U.S. Pat. Nos. 3,274,000 by Noe et al issued Sept. 20, 1966, 3,542,547 by Wilson issued Nov. 24, 1970, and 3,542,544 by Seus et al issued Nov. 24, 1970;

(3) 4-diarylamino-substituted chalcones of the types described by Fox, U.S. Pat. No. 3,526,501 issued Sept. 1, 1970;

(4) nonionic cycloheptenyl compounds of the types described by Looker, U.S. Pat. No. 3,533,786 issued Oct. 13, 1970;

(5) compounds containing an:

>N—N< nucleus, as described by Fox, U.S. Pat. No. 3,542,546 issued Nov. 24, 1970;

(6) organic compounds having a 3,3'-bisaryl-2-pyrazoline nucleus, as described by Fox et al, U.S. Pat. No. 3,527,602 issued Sept. 8, 1970;

(7) triarylamines in which at least one of the aryl radicals is substituted by either a vinyl radical or a vinylene radical having at least one active hydrogen-containing group, as described by Brantly et al, U.S. Pat. No. 3,567,450 issued Mar. 2, 1971;

(8) triarylamines in which at least one of the aryl radicals is substituted by an active hydrogen-containing group, as described by Brantly et al, Belgian Pat. No. 728,563 dated Apr. 30, 1969;

(9) any other organic donor compound which exhibits photoconductive properties such as those set forth in Australian Pat. No. 248,402 and the various polymeric photoductors such as the photoconductive carbazol polymers described in U.S. Pat. No. 3,421,891 issued Jan. 14, 1969.

Binders for use in preparing photoconductive layers comprise polymers having high dielectric strength which are good electrically insulating film-forming vehicles.

Useful materials include styrene-butadiene copolymers; silicone resins; styrene-alkyd resins; silicone-alkyd resins; soyaalkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetals) such as poly(vinyl butyral); polyacrylic and methacrylic esters such as poly(methyl methacrylate), poly(n-butyl methacrylate), poly(isobutyl methacrylate), etc.; polystyrene; nitrated polystyrene; polymethylstyrene; isobutylene polymers; polyesters such as poly(ethylene alkylenebis(aryleneoxyalkylene)terephthalate) such as poly[ethylene-co-2,2'-isopropylidenebis(phenyleneoxyethylene)]-terephthalate; phenolformaldehyde resins; ketone resins; polyamides; polycarbonates; polythiocarbonates; nuclear-substituted poly(vinyl haloarylates), etc.

Suitable resins are sold under such trademarks as Vitel TM PE-101, Cymac TM, Piccopale TM 100, Saran TM F-220 and Lexan TM 105 and 145.

The organic coating solvents useful for preparing coating dopes are selected from a variety of materials. Useful liquids are hydrocarbon solvents, including substituted hydrocarbon solvents, with preferred materials being halogenated hydrocarbon solvents. The requisite properties of the solvent are that it be capable of dissolving the acceptor and capable of dissolving, or at least highly swelling or solubilizing the polymeric ingredient of the composition. In addition, it is helpful if the solvent is volatile, preferably having a boiling point of less than about 200° C. Particularly useful solvents include halogenated lower alkanes having from 1 to about 3 carbon atoms such as dichloromethane, dichloroethane, dichloropropane, trichloromethane, trichloroethane, tribromomethane, trichlorofluoromethane, trichlorotrifluoroethane, etc.; aromatic hydrocarbons such as benzene, toluene, as well as halogenated benzene compounds such as chlorobenzene, bromobenzene, dichlorobenzene, etc.; ketones such as dialkyl ketones having 1 to about 3 carbon atoms in the alkyl moiety such as dimethyl ketone, methyl ethyl ketone, etc.; and ethers such as tetrahydrofuran, etc. Mixtures of these and other solvents are also useful.

In preparing the photoconductive coating composition, useful results are obtained where the donor is present in an amount equal to at least about 1 weight percent of the coating composition. The upper limit in the amount of donor present is widely varied in accordance with usual practice. In those cases where a binder is employed, it is generally required that the donor be present in an amount from about 1 weight percent of the coating composition to about 99 weight percent of the coating composition. A polymeric donor can be employed, in which case an additional binder may not be required. A preferred weight range for the donor substance in the coating composition is from about 10 weight percent to about 60 weight percent.

Suitable supporting materials for coated photoconductive layers which are sensitized in accordance with the method of this invention can include any of a wide variety of electrically conducting supports, for example, paper (at a relative humidity above 20 percent); aluminum-paper laminates; metal foils such as aluminum foil and zinc foil; metal plates such as aluminum, copper, zinc, brass and galvanized plates; vapor-deposited metal layers such as silver, nickel and aluminum coated on paper or conventional photographic film bases such as cellulose acetate and polystyrene. Such conducting materials as nickel can be vacuum-deposited on transparent film supports in sufficiently thin layers to allow photoconductive elements prepared therewith to be exposed from either side of such elements. An especially useful conducting support is prepared by coating a support material such as poly(ethylene terephthalate) with a conducting layer containing a semiconductor dispersed in a resin. Such conducting layers both with and without insulating barrier layers are described in U.S. Pat. No 3,245,833. Likewise, a suitable conducting coating can be prepared from the sodium salt of a carboxyester lactone of maleic anhydride and a vinyl acetate polymer. Such kinds of conducting layers and methods for their optimum preparation and use are disclosed in U.S. Pat. Nos. 3,007,901 and 3,262,807.

Coating thicknesses of the photoconductive composition on the support can vary widely. Generally, a coating in the range of about 10 microns to about 300 microns before drying is useful for the practice of this invention. The preferred range of coating thickness is found to be in the range from about 50 microns to about 150 microns before drying, although useful results are obtained outside this range. The resultant dry thickness of the coating is preferably between about 2 microns and about 50 microns, although useful results are obtained with a dry coating thickness between about 1 and about 200 microns.

The photoconductive compositions are employed in any of the well-known photoconductive processes which require photoconductive layers and elements. In one such process, a photoconductive element is held in the dark and given a blanket electrostatic charge by placing it under a corona discharge. This uniform charge is retained by the layer because of the substantial dark insulating property of the layer, i.e., the low conductivity of the layer in the dark. The electrostatic charge formed on the surface of the photoconductive layer is then selectively dissipated from the surface of the layer by imagewise exposure to light by means of a conventional exposure operation, for example, by a contact-printing technique, or by lens projection of an image to form a latent electrostatic image in the photoconductive layer. Exposing the surface in this manner forms a pattern of electrostatic charge by virtue of the fact that light energy striking the photoconductor causes the electrostatic charge in the light-struck areas to be conducted away from the surface in proportion to the intensity of the illumination in a particular area.

The charge pattern produced by exposure is then developed or transferred to another surface and developed there, i.e., either the charged or uncharged areas rendered visible, by treatment with a medium comprising electrostatically responsive particles having optical density. The developing electrostatically responsive particles can be in the form of a dust, i.e., powder, or a pigment in a resinous carrier, i.e., toner. A preferred method of applying such toner to a latent electrostatic image for solid area development is by the use of a magnetic brush. Methods of forming and using a magnetic brush toner applicator are described in U.S. Pat. Nos. 2,786,439 by Young, 2,786,440 by Giaimo and 2,786,441 by Young, all issued Mar. 26, 1957, and 2,874,063 by Greig issued Feb. 17, 1959. Liquid development of the latent electrostatic image is also useful. In liquid development, the developing particles are carried to the image-bearing surface in an electrically insulating liquid carrier. Methods of development of this type are widely known and have been described in the patent literature, for example, Metcalfe et al, U.S. Pat. No. 2,907,674 issued Oct. 6, 1959. In dry developing processes, the most widely used method of obtaining a permanent record is achieved by selecting a developing particle which has as one of its components a low-melting resin. Heating the powder image then causes the resin to melt or fuse into or on the element. The powder is, therefore, caused to adhere permanently to the surface of the photoconductive layer. In other cases, a transfer of the electrostatic charge image formed on the photoconductive layer is made to a second support such as paper which then becomes the final print after development and fusing. Techniques of the type indicated are well-known in the art and have been described in the literature in RCA Review, Volume 15 (1954), pages 469–484.

The following illustrative examples show the use of the dyes of the present invention as sensitizers in electrophotographic elements.

EXAMPLES 19–39

Each film was formulated and coated as follows. Ten to fifteen mg of a dye from Table I and 215 mg to 300 mg of tri-p-tolylamine were dissolved in 3 ml of dichloromethane. To this solution were added 4 ml of dichloromethane containing 12.5% Lexan ™ 145 (a bisphenol polycarbonate available from General Electric) by weight. The solution was stirred for several minutes and then coated at 0.006 mil wet thickness on a poly(ethylene terephthalate) support containing 0.4 OD evaporated nickel. After initial evaporation of the solvent, the films were dried 24 hours in air at 60° C. Dry thickness was about 7 μm.

The quantum efficiency ($\Phi_0$) of each film was measured as follows. Samples were coronacharged to a surface potential equivalent to the field strengths, $E_0$. They were then exposed to monochromatic radiation at the wavelength of maximum absorption with a bandwidth of 10 nm. The incident photon flux at this wavelength was measured with a radiometer. Films were allowed to discharge while exposed to the indicated radiation. The initial quantum efficiency (the number of electron-hole pairs produced per incident photon) at field strength $E_0$ was then determined by computation of the slope of the discharge curve at $E_0$. The photodischarge sensitivity at wavelength of irradiation ($S_{\frac{1}{2}}$), was also determined by allowing the films to discharge from $E_0$ to $E_0/2$. The amount of radiation necessary to produce this discharge was then calculated from the time required for this half-decay and the incident photon flux.

Compounds 1–20 and 22–23 of Table I were tested as described above. Each of the dyes resulted in an increase in the speed and/or quantum efficiency of the photoconductive layers in which they were included.

TABLE II

Initial Quantum Efficiencies ($\Phi_0$) and Photosensitivities ($S_{\frac{1}{2}}$) for Tri-p-tolylamine-Lexan 145 Films Containing 1 to 2% 4H—Tellurin Tellurane Sensitizers

| Compound | E V/cm | $\Phi_0$ | $S_{\frac{1}{2}}$ erg/cm$^2$ |
|---|---|---|---|
| none | 1.6 × 10$^6$ | 0.0094 | 1500 |
| 1 | 1.0 × 10$^6$ | 0.087 | 42 |
| 4 | 1.0 × 10$^6$ | 0.128 | 32 |
| 5 | 1.0 × 10$^6$ | 0.086 | 52 |
| 6 | 1.0 × 10$^6$ | 0.054 | 90 |
| 7 | 1.0 × 10$^6$ | 0.057 | 87 |
| 8 | 9.9 × 10$^5$ | 0.121 | 43 |
| 9 | 7.7 × 10$^5$ | 0.090 | 47 |
| 10 | 8.7 × 10$^5$ | 0.100 | 51 |
| 11 | 1.0 × 10$^6$ | 0.138 | 36 |
| 14 | 1.0 × 10$^6$ | 0.045 | 145 |
| 16 | 1.0 × 10$^6$ | 0.013 | 392 |
| 17 | 1.0 × 10$^6$ | 0.052 | 101 |
| 19 | 1.0 × 10$^6$ | 0.04 | 263 |
| 20 | 1.0 × 10$^6$ | 0.04 | 294 |
| 22 | 5 × 10$^5$ | 0.065 | 110 |
| 23 | 5 × 10$^5$ | 0.057 | 87 |

The invention has been described in detail with particular reference to preferred embodiments thereof, but it will be understood that variations and modifications can be effected within the spirit and scope of the invention.

We claim:

1. A compound having the structure

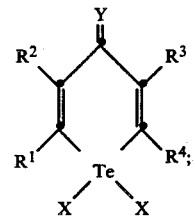

wherein
R$^1$ and R$^4$, each independently represent hydrogen, alkyl, trialkylsilyl, triarylsilyl, alkylarylsilyl, aryl and heteroaryl;
R$^2$ and R$^3$, each independently represent hydrogen; or
R$^1$ and R$^2$, or R$^3$ and R$^4$ taken together with the carbon atoms to which they are attached, form a 4 to 20 carbon atom mono- or polynuclear fused carbocyclic aromatic ring having at least one electron donating substituent meta to the carbon bearing the tellurium atom;

X represents F, Cl, Br, I, OH,

wherein R$^5$ represents alkyl or aryl;
Y represents O, S, C(CN)$_2$,

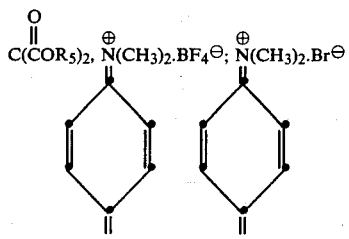

or a 4H-tellurin-4-ylidene group of the structure

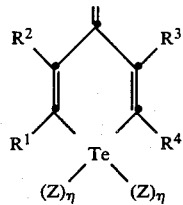

wherein $R^1$, $R^2$, $R^3$ and $R^4$ are as above;
Z represnets OH, or

and
η represents 0 or 1.

2. The compound of claim 1 wherein
$R^1$ and $R^4$, each independently, represents hydrogen, t-butyl or phenyl;
$R^2$ and $R^3$, each independently, represents hydrogen; or
$R^3$ and $R^4$ taken together with the carbons to which they are attached form a fused methoxysubstituted benzo group;
Y represents —C(CN)$_2$, O,

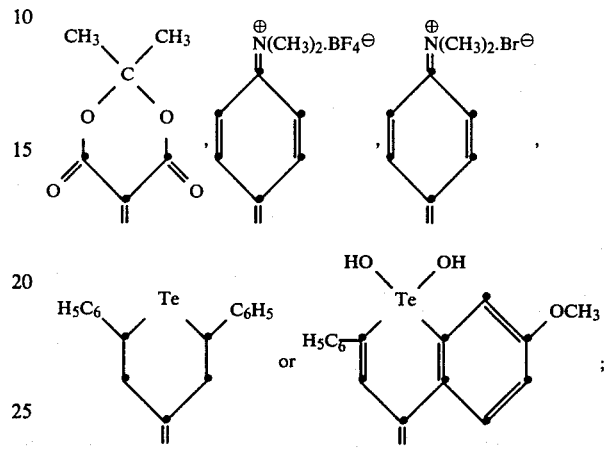

X represents Br, Cl, I, =O, OH, or

3. The compound of claim 1 selected from those compounds presented in Table I as follows:

TABLE I

4H—Tellurin Telluranes of the Following Structure

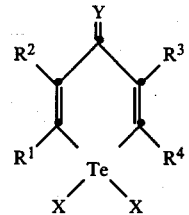

| Compound | $R^1$ | $R^2$ | $R^3$ | $R^4$ | X | Y |
|---|---|---|---|---|---|---|
| 1 | t-butyl | H | H | t-butyl | CH$_3$C(=O)—O | O |
| 2 | phenyl | H | H | phenyl | CH$_3$C(=O)—O | O |
| 3* | phenyl | H | | 7-methoxybenzo | CH$_3$C(=O)—O | O |
| 4 | t-butyl | H | H | t-butyl | CH$_3$C(=O)—O | C(CN)$_2$ |
| 5 | t-butyl | H | H | t-butyl | Br | O |
| 6 | phenyl | H | H | phenyl | Br | O |
| 7* | phenyl | H | | 7-methoxybenzo | Br | O |
| 8* | t-butyl | H | | 7-methoxybenzo | Br | O |
| 9 | t-butyl | H | H | t-butyl | Br | C(CN)$_2$ |
| 10 | phenyl | H | H | phenyl | Br | C(CN)$_2$ |

TABLE I-continued
4H—Tellurin Telluranes of the Following Structure

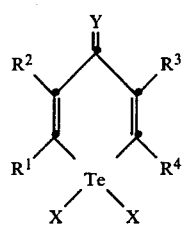

| Compound | R¹ | R² | R³ | R⁴ | X | Y |
|---|---|---|---|---|---|---|
| 11 | t-butyl | H | H | t-butyl | Br | (CH₃)₂C(O-)₂ with two C=O groups (Meldrum-type) |
| 12* | t-butyl | H | | 7-methoxybenzo | Br | (CH₃)₂C(O-)₂ with two C=O groups |
| 13 | phenyl | H | H | p-FC₆H₄ | Br | O |
| 14 | t-butyl | H | H | t-butyl | Cl | O |
| 15 | t-butyl | H | H | t-butyl | Cl | C(CN)₂ |
| 16 | t-butyl | H | H | t-butyl | I | O |
| 17 | t-butyl | H | H | t-butyl | I | C(CN)₂ |
| 18* | phenyl | H | | 7-methoxybenzo | Cl | O |
| 19 | phenyl | H | H | phenyl | O (=S/=O, double-bonded) | diphenyl telluranyl-substituted tellurone |
| 20* | phenyl | H | | 7-methoxybenzo | OH | Ph/OCH₃-substituted dihydroxytelluranyl |
| 21 | phenyl | H | H | trimethylsilyl | Br | O |
| 22 | phenyl | H | H | phenyl | Br | =C₆H₄—N(CH₃)₂·BF₄⁻ |

TABLE I-continued

4H—Tellurin Telluranes of the Following Structure

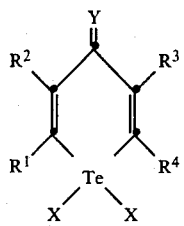

| Compound | R¹ | R² | R³ | R⁴ | X | Y |
|---|---|---|---|---|---|---|
| 23 | t-butyl | H | H | t-butyl | Br | $\overset{\oplus}{N}(CH_3)_2 \cdot Br^{\ominus}$ on a phenyl ring carbonyl |
| 24 | phenyl | H | H | triphenylsilyl | Br | O |
| 25 | phenyl | H | H | dimethylphenylsilyl | Br | O |

*These are compounds in which R³ and R⁴ taken together with the carbon atoms to which they are attached form a fused methoxybenzo group in which the methoxy group is meta to the carbon atom to which the Te atom is attached or more specifically, in the 7-position of the resulting 4H—tellurium nucleus.

4. A photoconductive composition comprising an electron-donating organic photoconductor and a sensitizing amount of a compound defined in any one of claims 1, 2 or 3, 5. A photoconductive composition as in claim 4 wherein the sensitizing compound is present in an amount of from 0.001 to 30 percent based on the weight of the composition.

6. A photoconductive composition as in claim 4 wherein the electron-donating photoconductor comprises a tertiary amine.

7. A photoconductive composition as in claim 4 wherein the electron-donating photoconductor comprises a triarylamine.

8. A photoconductive composition as in claim 4 wherein the electron-donating photoconductor is tri-p-tolylamine.